(12) United States Patent
Schaumann et al.

(10) Patent No.: US 12,357,363 B2
(45) Date of Patent: Jul. 15, 2025

(54) PERCUTANEOUS TARGETING DEVICE

(71) Applicant: ARTHREX, INC., Naples, FL (US)

(72) Inventors: Michael Schaumann, Munich (DE);
Rebecca Weschenfelder, Stoffen (DE);
Jörg Mietzner, Wolfratshausen (DE);
Victor Dubois-Ferrière, Carouge (CH);
Zack Day, Naples, FL (US); Jorge Acevedo, Jacksonville, FL (US)

(73) Assignee: ARTHREX, INC., Naples, FL (US)

( * ) Notice: Subject to any disclaimer, the term of this patent is extended or adjusted under 35 U.S.C. 154(b) by 102 days.

(21) Appl. No.: 17/890,350

(22) Filed: Aug. 18, 2022

(65) Prior Publication Data
US 2023/0000506 A1  Jan. 5, 2023

Related U.S. Application Data

(63) Continuation of application No. 17/885,803, filed on Aug. 11, 2022, which is a continuation of application
(Continued)

(30) Foreign Application Priority Data

Jun. 20, 2018  (EP) .................................. 18178849

(51) Int. Cl.
*A61B 17/90* (2006.01)
*A61B 17/17* (2006.01)
(Continued)

(52) U.S. Cl.
CPC .......... *A61B 17/90* (2021.08); *A61B 17/1775* (2016.11); *A61B 17/56* (2013.01);
(Continued)

(58) Field of Classification Search
CPC ... A61B 17/151; A61B 17/17; A61B 17/1775; A61B 17/1782; A61B 17/56;
(Continued)

(56) References Cited

U.S. PATENT DOCUMENTS

| 4,672,957 A | 6/1987 | Hourahane |
| 5,891,150 A * | 4/1999 | Chan ................... A61B 17/1714 606/98 |

(Continued)

FOREIGN PATENT DOCUMENTS

| EP | 2561815 | 2/2013 |
| FR | 2911264 | 7/2008 |

(Continued)

OTHER PUBLICATIONS

International Search Report and Written Opinion for International application No. PCT/US2019/038116 dated Sep. 20, 2019.
(Continued)

*Primary Examiner* — Larry E Waggle, Jr.
(74) *Attorney, Agent, or Firm* — Carlson, Gaskey & Olds, P.C.

(57) ABSTRACT

A percutaneous targeting device comprises a body holding an extension. The body has a target guide holding a target pin which may be a K-wire. The extension has two guide sleeves, holding a guide wire. All wires are held in a common plane. The guide wires serve as a guide for cannulated fixation screws. The extension is movable against the body to adjust the angle between the target pin and the guide wires.

19 Claims, 7 Drawing Sheets

Related U.S. Application Data

No. 17/252,865, filed as application No. PCT/US2019/038116 on Jun. 20, 2019, now abandoned.

(51) Int. Cl.
*A61B 17/56* (2006.01)
*A61B 17/84* (2006.01)
*A61B 17/88* (2006.01)
*A61B 90/11* (2016.01)

(52) U.S. Cl.
CPC ........ *A61B 17/848* (2013.01); *A61B 17/8897* (2013.01); *A61B 90/11* (2016.02); *A61B 2017/565* (2013.01)

(58) Field of Classification Search
CPC ............ A61B 2017/565; A61B 17/848; A61B 17/8897; A61B 17/90
See application file for complete search history.

(56) References Cited

U.S. PATENT DOCUMENTS

| | | |
|---|---|---|
| 8,617,176 B2 | 12/2013 | Lizardi et al. |
| 8,663,233 B2 | 3/2014 | Suda |
| 8,821,504 B2 | 9/2014 | Sharkey et al. |
| 9,265,878 B2* | 2/2016 | McGhie ................ A61M 5/008 |
| 9,498,370 B2 | 11/2016 | Taylor et al. |
| 11,439,412 B2* | 9/2022 | Woodard ........... A61B 17/1725 |
| 2002/0133165 A1 | 9/2002 | Whittaker et al. |
| 2009/0036931 A1 | 2/2009 | Pech et al. |

FOREIGN PATENT DOCUMENTS

| | | |
|---|---|---|
| JP | H11267135 | 10/1999 |
| JP | 2013043093 | 3/2013 |
| WO | 00/25681 | 5/2000 |
| WO | 2014/013517 | 1/2014 |

OTHER PUBLICATIONS

International Preliminary Report on Patentability for International application No. PCT/US2019/038116 dated Dec. 30, 2020.

* cited by examiner

PERCUTANEOUS TARGETING DEVICE

REFERENCE TO RELATED APPLICATIONS

This application is a continuation of U.S. patent application Ser. No. 17/885,803 filed Aug. 11, 2022, which is a continuation of U.S. patent application Ser. No. 17/252,865 filed Dec. 16, 2020, which is a United States National Phase application of PCT Application No. PCT/US2019/038116 filed Jun. 20, 2019, which claims priority to European Patent Application No. 18178849.8 filed on Jun. 20, 2018.

BACKGROUND

This disclosure relates to a percutaneous targeting device which may be used in a chevron osteotomy procedure.

A hallux valgus deformity is a common foot disorder that can result in the formation of a bunion on a patient's foot. A known procedure for the correction of a hallux valgus deformity is the minimal-invasive chevron osteotomy procedure. After performing the chevron osteotomy, bone fragments are realigned and fixed by fixation screws. The screws may be inserted by the surgeon in a minimally invasive fashion in an oblique angle into the bone. For correct placement of the screws, a large number of X-ray images is required which may result in loss of time, a large radiation dose, and costs.

SUMMARY

Disclosed herein are guides to aid in screw placement for minimally invasive foot surgery (e.g., bunion surgery—Chevron and/or Akin osteotomies). Devices herein ease guide wire (e.g., (Kirschner-wire, also known as a K-wire) placement for screw fixation (e.g., cannulated screw)

The percutaneous targeting device, herein also mentioned as tool, according to the embodiments allows simple and precise targeting for the placement of screws to secure bone fragments of small bones. After a target pin has been placed in a bone (which may be made by a drill or similar tool) and the tool is placed on the reference pin, the tool ensures that the screws are in a plane through the target pin. Due to markings and/or a window, the length of the target pin can easily be adjusted such that the target pin ends within a target window or at an intersect point.

Location of a plane can easily be checked by a surgeon by considering the position of the body and the target pin. For better indicating the plane, the body may have a flat shape. The tool can be adjusted by moving the extension relative to the body, such that the angle between the target pin and the guide pins can be adapted to specific needs. Independent of this adjustment, the guide pins remain parallel. If one of the guide pins is fixed to the bone (which may be made by a drill or similar tool), the tool is fixed in its position relative to the bone. The second or any further guide pins are forced to be parallel to the first guide pin. Therefore, oblique screws and the weakening of bone material are prevented. The length of the guide pins is indicated by markings at the tool. The length of the first guide pin to contact with its tip the tip of the target pin is always the same if the target pin has been adjusted with respect to the tool or vice-versa as mentioned above. The indicated lengths allow a calculation of the required screw lengths.

A method of fixing bone fragments in minimally invasive foot surgery comprises using a percutaneous targeting device. The targeting device with the target guide can be positioned on the target pin, such that the target pin is guided within the target guide. Positioning may be done such that a visible mark at the target pin is aligned with the body of the target guide or a marking thereof. Alternatively, the sleeve of the target guide may be positioned over the target pin and the targeting device body may be attached later to the target guide. After performing the osteotomy, the hook of a hook sleeve assembly may be inserted intramedullary into the proximal part of the metatarsal bone. A first guide wire may be placed through a positioning screw of the hook sleeve assembly and the hook sleeve into the distal part of the metatarsal bone. The distal part of the metatarsal bone may be shifted/positioned by rotating the positioning screw along the guide wire. The tip of the positioning screw may be in direct contact with the distal bone fragment or may push the fragment through the skin (via a plunger tip). Additionally, a first guide sleeve may be inserted into the outmost attachment hole and at least a further guide sleeve may be inserted into one of the other attachment holes. Then, the tool can be adjusted by moving the extension such that the guide sleeves or guide wires are under a desired angle relative to the target pin. This allows a precise selection of the screw angle in the bone.

By these methods, multiple screws are precisely parallel. The length of the screws can be selected based on the lengths of the first guide wire and the second guide wire extending into the bone. Therefore, perforating two surfaces of the bone by screws that are too long can be prevented.

DETAILED DESCRIPTION

Figure 1:
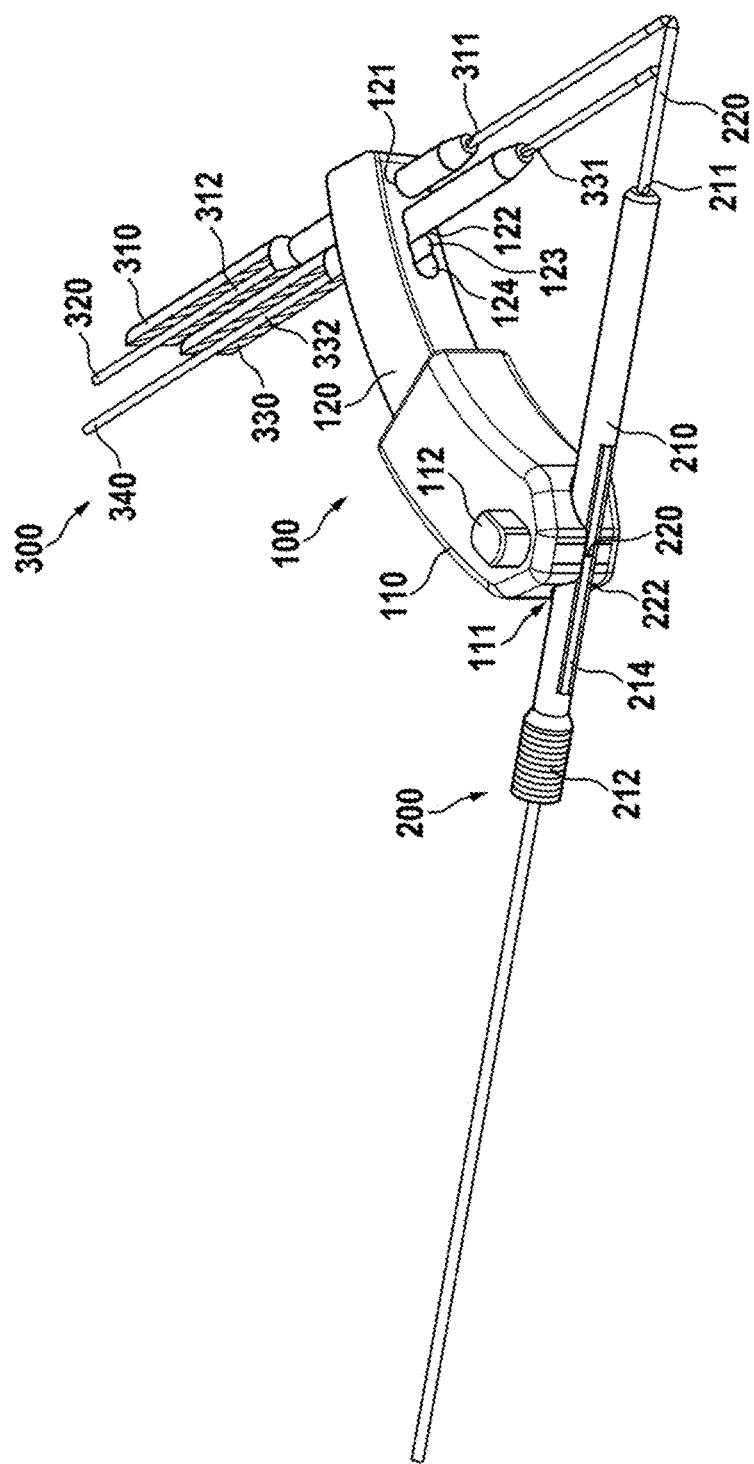
FIG. 1 shows a targeting device.

Embodiments of devices disclosed herein simplify the placement of fixation screws in a bone of distal extremities, which can be problematic during such surgical procedures. For example, fixation of metatarsal bone fragments is simplified using the devices as described herein after a minimally invasive chevron osteotomy procedure.

In a first embodiment, a percutaneous targeting device for minimal invasive foot surgery comprises a body holding an extension. The body has attachment means for a target guide comprising a target sleeve for holding a target pin. Additionally or alternatively, a hook sleeve or hook sleeve assembly having a sideward hook may be used. The extension has multiple attachment holes for holding at least one guide wire and/or at least one guide sleeve. The at least one guide sleeve may further hold a guide wire. The guide sleeves give a better guidance and a higher stability to the guide wires. The target sleeve is configured for holding a target pin, which may be a K-wire. The target pin may extend axially through the target sleeve. The target sleeve may be configured to hold the target pin in a fixed position relative to the target sleeve. If required, the target pin may be released from its fixed position. The target pin may be movable within the target sleeve, in a direction, which may be along its longitudinal axis. This may allow to position the target pin and/or to insert/remove the target pin. The guide sleeves may be configured for holding guide wires. A K-wire is a wire having a tip and configured to be drilled into a bone. The guide wires may have a tip and may be configured to be drilled into a bone. Any of the guide wires may be a K-wire. The target pin and the guide wires may have a diameter between 5 mm and 0.5 mm or between 3 mm and 1 mm A first attachment hole for holding a first guide sleeve or a first guide wire is located out most of the extension and therefore most distant from the target sleeve. Further attachment holes for holding further guide sleeves or guide Wires may be parallel to the first attachment hole and closer to the target sleeve. The extension may be movable against the body and may be held slidably in the body to extend the distance and/or angle between the target sleeve and the guide sleeves. The target sleeve and the guide sleeves and/or the guide wires may be in a common plane and point into a common target area. Therefore, wires held by the target sleeve and the guide sleeves may be in the same plane and when inserted correctly, their tips may end within the target area.

The target sleeve may have a tubular shape forming a target sleeve channel. The first guide sleeve may have a tubular shape forming a first guide sleeve channel. A second guide sleeve may have a tubular shape forming a second guide sleeve channel. The other guide sleeves may have a tubular shape, and the guide sleeves forming a guide sleeve channel. The channels may have an inner bore adapted to the outer diameter of the wires they are used for. The target guide may be adapted to fit to the body and the guide sleeves may be adapted to fit into the attachment holes. The guide sleeves may have marks or rules which may indicate the depth of wires held by the guide sleeves. For this purpose, the wires may have visible marks such as laser marks.

The body and the extension may be arc-shaped. The arc-shaped body may define a first radial axis and the arc-shaped extension may define a second radial axis. The first radial axis and the second radial axis may intersect at an intersect point within the target area. The target sleeve and one of the guide sleeves may also point to an intersect point within the target area which may be the same intersect point as mentioned above. The target area may be defined as a circular area centered on the intersect point. When sliding the extension in or out of the body, there may be an arched movement and the intersect point may not move, but the angle between the target sleeve channel and the first guide sleeve channel or a first guide wire, if the guide wire is held without sleeve, changes.

The target pin may have at least one visible mark which may be a laser mark in a predetermined distance from its tip. The target guide may have a window through which the target pin may be seen such that the visible mark at the target pin may be aligned with the body. For this purpose, the body may have an alignment mark. Alignment of the visible mark at the target pin with the body may ensure that the tip of the target pin is within the target area. In a further embodiment, the tip of the target pin may be at the intersect point. The target guide may also have a target sleeve which may have a coupling section, which may be threaded and by which it may be moved to position the metatarsal bone fragments. The target sleeve may have a gear rack which interfaces with a rack-wheel at the body and which allows movement of the target sleeve along a longitudinal axis of the target sleeve.

In a further embodiment, the body may be one piece with the extension or at least fixedly attached thereto. Angular adjustment may be made by selecting attachment holes which result in a required angle between the target pin and the at least one guide wire.

The percutaneous targeting device, herein also mentioned as tool, according to the embodiments allow simple and precise targeting for the placement of screws to secure bone fragments of small bones. After the target pin has been placed in a bone (which may be made by a drill or similar tool) and the tool is placed on the reference pin, the tool ensures that the screws are in a plane through the target pin. Due to markings and/or a window, the length of the target pin can easily be adjusted such that the target pin ends within a target window, or even at an intersect point.

The location of the plane can easily be checked by a surgeon by considering the position of the body and the target pin. For better indicating the plane, the body may have a flat shape. The tool can be adjusted by moving the extension relative to the body, such that the angle between the get pin and the guide pins can be adapted to specific needs. Independent of this adjustment, the guide pins remain parallel. If one of the guide pins is fixed to the bone (which may be made by a drill or similar tool), the tool is fixed in its position relative to the bone. The second or any further guide pins may be forced to be parallel to the first guide pin. Therefore, oblique screws and the weakening of bone material are prevented. The length of the guide pins is indicated by markings at the tool. The length of the first guide pin to contact with its tip the tip of the target pin is always the same if the target pin has been adjusted with respect to the tool or vice-versa as mentioned above. The indicated lengths allow a calculation of the required screw lengths.

Finally, the screws, (e.g., cannulated fixation screws) may be inserted over the guide wires. The instrument can easily be removed by removing one wire after the other.

A method of fixing bone fragments in minimally invasive foot surgery comprises placing a target pin, which may be a K-wire, in the distal part of a metatarsal bone. Then an osteotomy may be performed, and the distal bone part with the target pin may be repositioned. In a next step, the targeting device with the target guide may be positioned on the target pin, such that the target pin is guided within the target guide. Positioning may be done such that a visible mark at the target pin is aligned with the body of the target guide or a marking thereof. Alternatively, the sleeve of the target guide may be positioned over the target pin, and the targeting device body may be attached later to the target guide. In a further embodiment, after performing the osteotomy, the hook of a hook sleeve assembly may be inserted intramedullary into the proximal part of the metatarsal bone. A first target pin may be placed through a positioning screw of the hook sleeve assembly and the hook sleeve into the distal part of the metatarsal bone. The distal part of the metatarsal bone may be shifted/positioned by rotating the positioning screw along the target pin. The tip of the positioning screw may be in direct contact with the distal bone fragment or may push the fragment through the skin (e.g., via a plunger tip).

A first guide sleeve may be inserted into the outmost attachment hole and at least a further guide sleeve may be inserted into one of the other attachment holes. This step may also be performed before positioning the tool over the reference guide. The guide sleeves may also be pre-assembled. The tool can be adjusted by moving the extension such that the guide sleeves or guide wires may be under a desired angle relative to the target pin. This allows a precise selection of the screw angle in the bone.

Guide wires, e.g., two guide wires, may be inserted through the guide sleeves into the bone. Alternatively, at least one guide wire may be directly inserted through an attachment hole. In this embodiment, the step of inserting a guide sleeve can be omitted. The tip of the outmost guide wire in a first guide sleeve may contact the tip of the target pin within the target area or may even contact at the intersect point. The tip of other guide wires in other guide sleeves may contact a target pin within the target area. An intersection between the target pin and the first guide wire and/or an intersection between the target pin and the second guide wire may be outside of the target sleeve. The target pin and the guide wires may be all in the same plane. The guide wires may be inserted in any sequence. The first guide wire may be inserted first, followed by the second guidewire. Alternatively, the first guide wire may follow the second guide wire. It may also be possible to insert a guidewire first, followed by a target pin.

Any of the target pin, the first guide wire, and the second guide wire may define a center axis. In general, the center axis of the target pin may intersect with the center axis of the first guide wire and/or the center axis of the target pin may intersect with the center axis of the second guide wire. The center axis of the first guide wire may be parallel to the center axis of the second guide wire.

In an embodiment, the extension may be adjusted to bring the guide sleeve in a new position for another guide wire after inserting a first guide wire.

Cannulated fixation screws may be screwed into the bone by using the guide wires. The guide wires pass through the cannulations of the screws. The tool may be removed before or after screwing the fixation screws into the bone. At the end, the tool, the guide wires, and the target pin may be removed.

By these methods, multiple screws are precisely parallel. The length of the screws can be selected based on the lengths of the first guide wire and the second guide wire extending into the bone. Therefore, perforating two surfaces of the bone by screws that are too long can be prevented.

In FIG. 1, a first embodiment is shown. The percutaneous targeting device 100 comprises a body 110 and an extension 120. The extension may be movable with respect to the body 110 for angular adjustment. The body 110 has attachment means for a target guide 200. In an embodiment, the target guide 200 has a tubular target sleeve 210 with a target sleeve channel 211 having a diameter adapted to hold a target pin 220. There may be a hole or a cylindrical bore in the device body 110 to hold the target guide 200. There may also be locking means 112 at the device body 110 for fixing the target guide 200 at its position. The target guide 200 may be moveable within the body 110 and it may be removable from the body 110. The target guide 200 may also be fixed to the body 110 or one part with the body 110. It may further have a window 214 through which a mark 222 such as a laser mark at the target pin 220 can be seen aligned with the body 110 or a mark at the body 110 or a mark at the target guide 200. The target guide 200 may also have a coupling section 212 such as a threaded section by which it may be held by a handle for easier installation. A target pin 220 may be a K-wire having a tip and configured to be drilled into a bone.

The extension 120 may have multiple attachment holes for holding guide sleeves 310, 330. A guide sleeve 310, 330 may have a tubular body forming a channel 311, 331 for holding a guide wire. There may be a first attachment hole 121 at an outmost position, most distant from the target guide 200. There may be an attachment opening 125 including further attachment holes 122, 123, 124 with increasing distances from the first attachment hole, but closer to the target guide 200. The attachment holes 121, 122, 123, 124 may include cylindrical bores, but any other suitable form may be used. The attachment holes 122, 123, 124 may be so close to one another that there exist no sidewalls between the holes. There may be at least one guide sleeve 310 in the outmost or first attachment hole 121. There may be a second guide sleeve 330 in one of the other attachment holes 122, 123, 124. The guide sleeves 310, 330 may be moveable within the extension 120, and they may be removable from the extension 120.

An appropriate attachment hole 121, 122, 123, 124 may be selected depending on the desired distance from between a first guide wire 320 held by the first guide sleeve 310 to a second guide wire 340 held by the second guide sleeve 330. The guide wires 320, 340 may have a tip and may be configured to be drilled into a bone. The first guide wire 320, the second guide wire 340, and the target pin 220 may be all in the same plane. When extended properly, the tip of the target pin 220 may contact the tip of the first guide wire 320. The tip of the second guide wire 330 may contact the target pin 220 distant from its tip, but still in the same plane. Herein the term of the same plane may include deviations with a maximum of 5 mm, 2 mm, or 1 mm, for example.

The guide sleeves 310, 330 may have markings or depth scales 312, 332 to indicate the depth or length of an inserted guide wire 320, 340. For a precise length reading, the guide wires 320, 340 may also have marks, for example laser marks.

In an embodiment, the target sleeve channel 211, the first guide sleeve channel 311, and the second guide sleeve channel 331 may be configured such that the intersection between the target pin 220 and the first guide wire 320 and/or the intersection between the target pin 220 and the second guide wire 340 is outside of the target sleeve 210.

Figure 2:
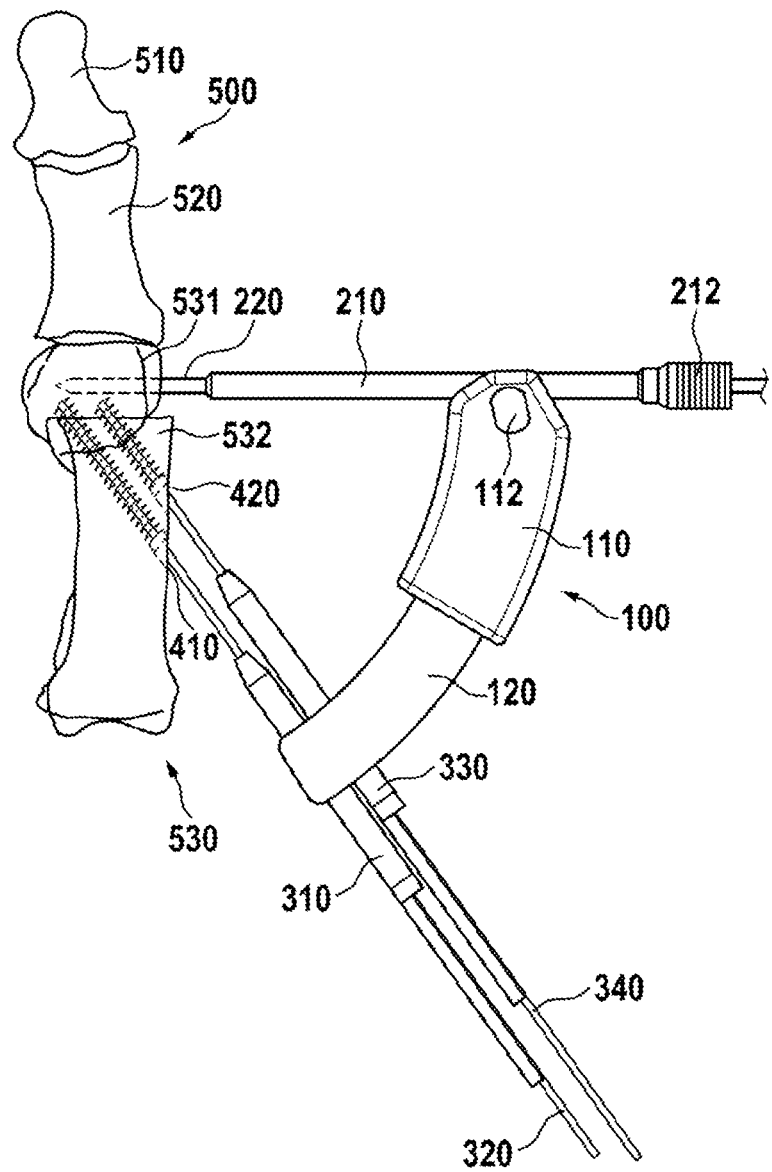
FIG. 2 shows the application of the targeting device at a bone.

In FIG. 2, the application of the targeting device 100 at a bone is shown. The big toe 500 comprises a metatarsal bone 530, a proximal phalanx 520, and a distal phalanx 510. The metatarsal bone 530 has been cut such that there exist two fragments 531, 532. These two fragments have to be screwed together in a new position as shown by two bone screws. Here, the target pin 220 is inserted into the metatarsal bone fragment 531 and holds the guide tool. A first guide wire 320 and a second guide wire 340 have already been inserted. A first cannulated screw 410 and a second cannulated screw 420 have already been screwed into the bone to fix the fragments 531 and 532 together.

Figure 3:
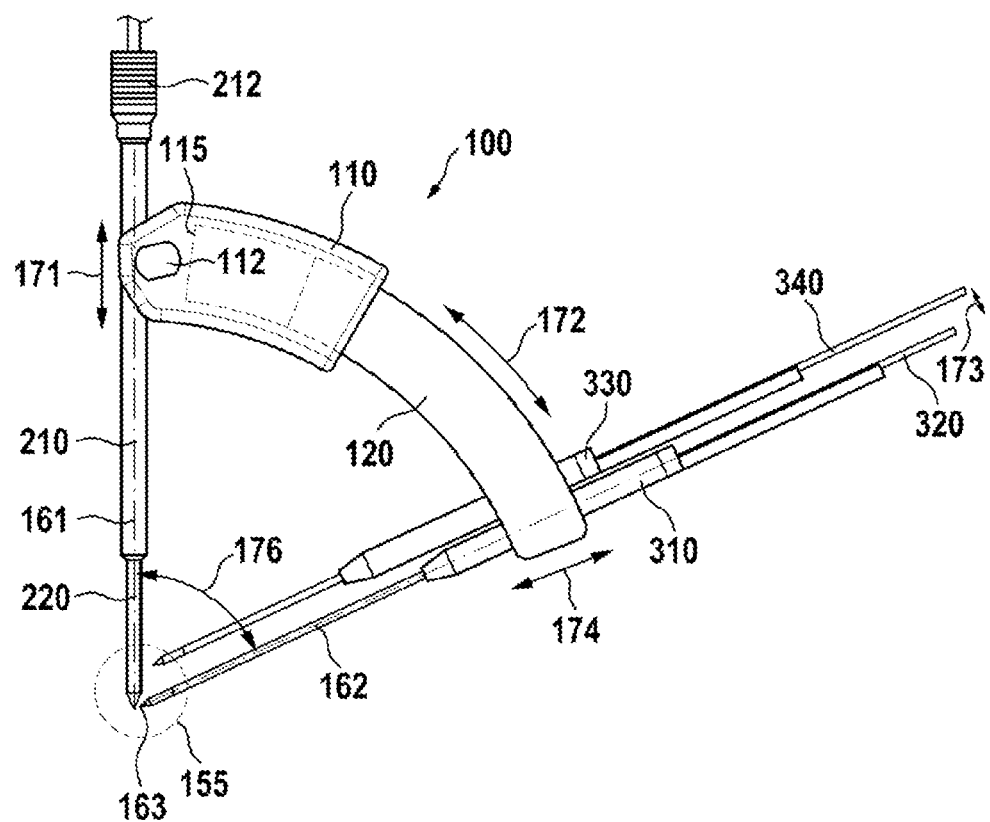
FIG. 3 shows details of the geometry and movement of the targeting device.

In FIG. 3, details of the geometry and movement of the targeting device are shown. The body 110 may be arc shaped and may have a hollow opening 115 to receive at least part of the extension 120, which also may be arc shaped. The extension 120 may be configured to move within device body 110. The extension 120 may be configured to move into a direction 172 relative to the body 110 for a rotational adjustment. This changes the rotation angle 176 between the center axis 161 of the target pin 220 and the center axis 162 of the first guide wire 320. The target pin 220 may be in fixed angular relationship with the device body 110 and the guide wires 320, 340 may be in fixed angular relationship with the device extension 120. The center axis 161 of the target pin 220 and the center axis 162 of the first guide wire 320 intersect within a target area 155 or even at an intersect point 163 independent of the relative position of the extension 120 relative to the body 110.

For size adjustment, the position of the target pin 220 may be adjusted in a direction 171 along its center axis 161. Depth adjustment may be made by moving any of the guide wires 320, 340 in a direction 174 along or parallel to the first guide wire 320 center axis 161. Distance adjustment of the guide wires 320, 340 may be made by a parallel movement of the guide wires into direction 173.

The target pin 220 and the first guide wire 320 may contact within the target area 155 or even at the intersect point 163. The target pin 220 and the second guide wire 340 may contact within the target area 155. The target area may be circular and have a diameter of 10 mm, 5 mm, or 2 mm, for example.

In an embodiment, the extension 120 may be configured to move relative to the body 110 such that the point of intersection between the target pin 220 and the first guide wire 320 does not move.

Figure 4:
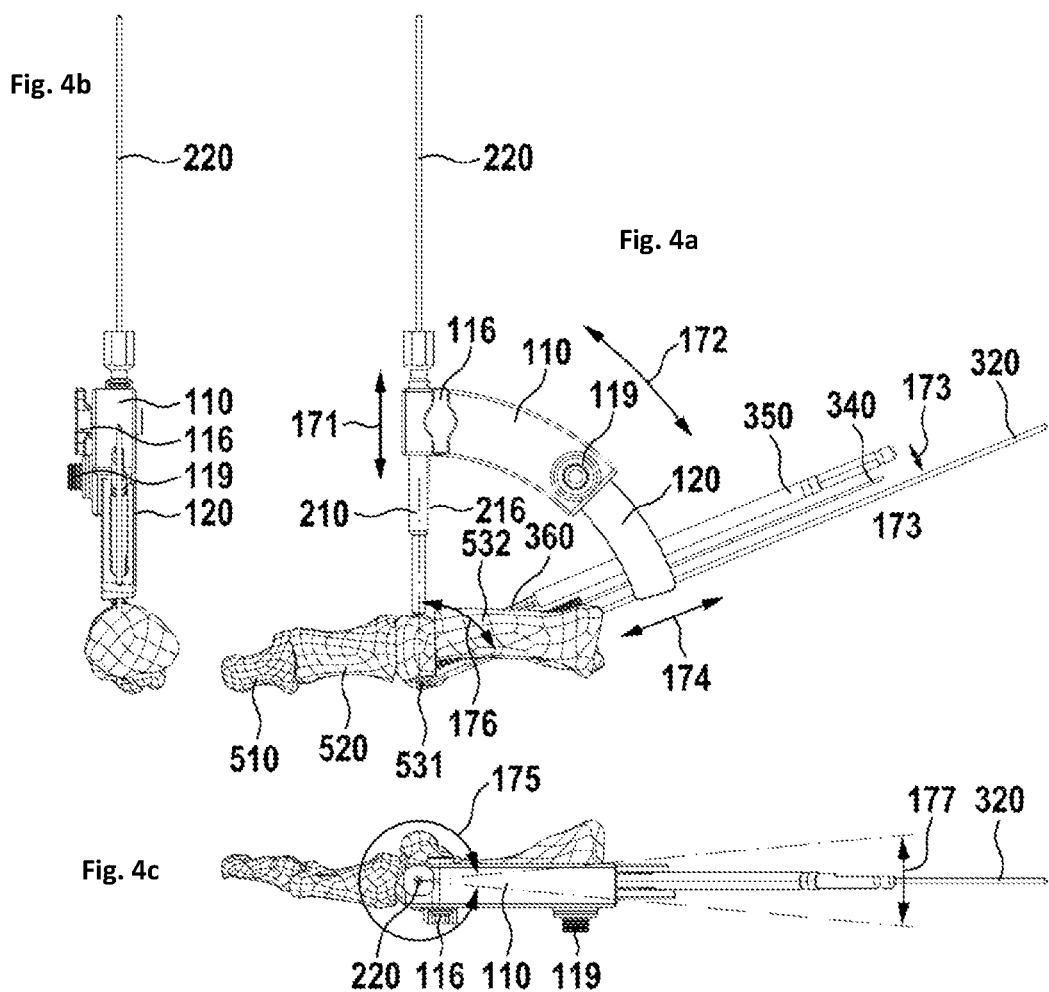
FIGS. 4a, 4b, and 4c show a further embodiment of the targeting device.

In FIGS. 4a, 4b, and 4c, a further embodiment is shown. Here, the first guide wire 320 and the second guide wire 340 may be held by the extension 120 without sleeves, and a third guide wire 360 may be held by a guide sleeve 350. The third guide wire 360 may be parallel to and in the same plane with the first guide wire 320 and the second guide wire 340. The center axis of the guide sleeves and/or the center axis of the guide wires may be in the same plane.

Figure 5:
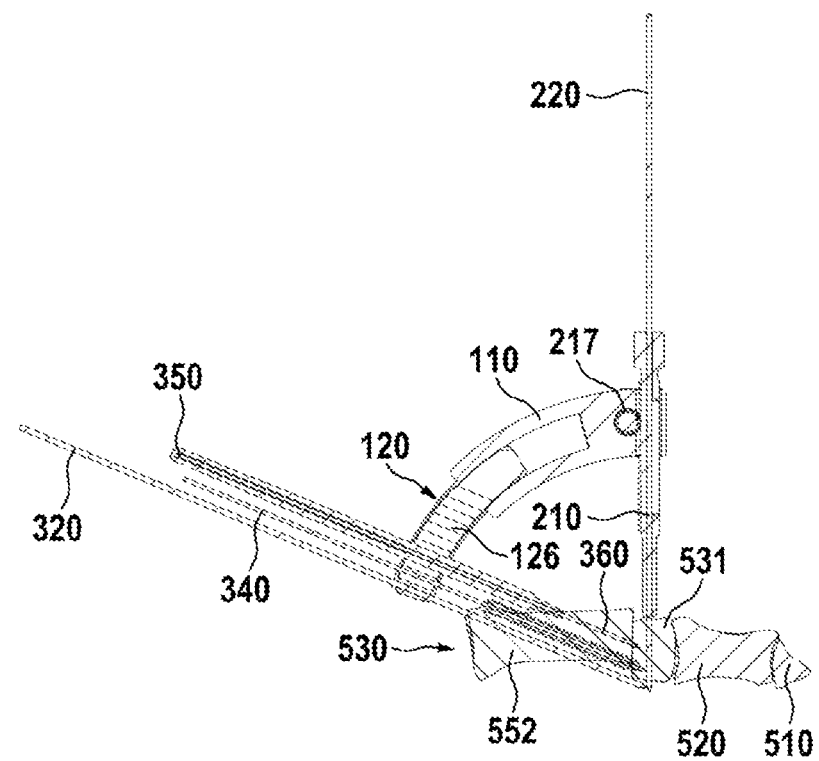
FIG. 5 shows a sectional view of the targeting device.

In this embodiment, the target sleeve 210 may have a gear rack 216 at one side which interfaces with a rack-wheel 217 shown in FIG. 5. The rack-wheel 217 may be driven by a handle 116. Rotation of the handle 116 may rotate the rack-wheel 217 and therefore move the gear rack 216 and the target sleeve 210 in and out.

There may be an extension lock 119 to lock the device extension 120 in a fixed relationship to the device body 110. The extension lock 119 may be a button which releases the device extension 120 when pressed, such that the device extension 120 may be moved relative to the device body 110.

The features of the embodiments shown herein may be combined in any combination.

Before inserting any guide wire into the bone, the targeting device may be rotated around the target pin 220 in a direction 175 which results in an angulation in an angulation angle 177.

FIG. 4a shows a front view, FIG. 4b shows a right side view, and FIG. 4c shows a top view of the embodiment.

FIG. 5 shows a sectional view of the targeting device.

In this embodiment, any guide wire 320, 340, 360 may be directly held by the device extension 120 without using a guide sleeve 310, 330, 350. For this purpose, a holding structure 126 may be in the device extension 120. This holding structure 126 may include holes, ribs, wedges or other elements forming attachment holes which may be adapted to hold guide wires and/or sleeves.

Figure 6:
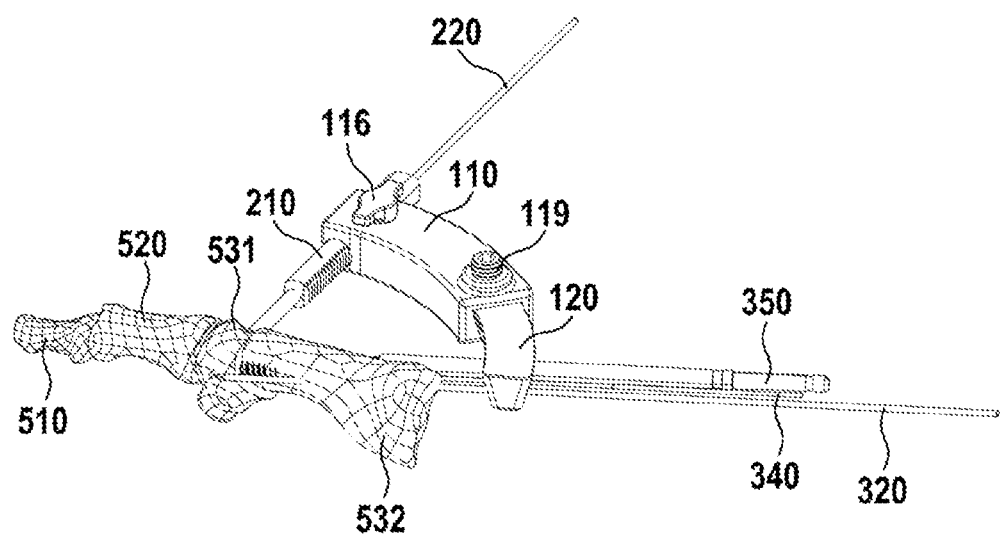
FIG. 6 shows a perspective view of the targeting device.

FIG. 6 shows a perspective view of the targeting device.

Figure 7:
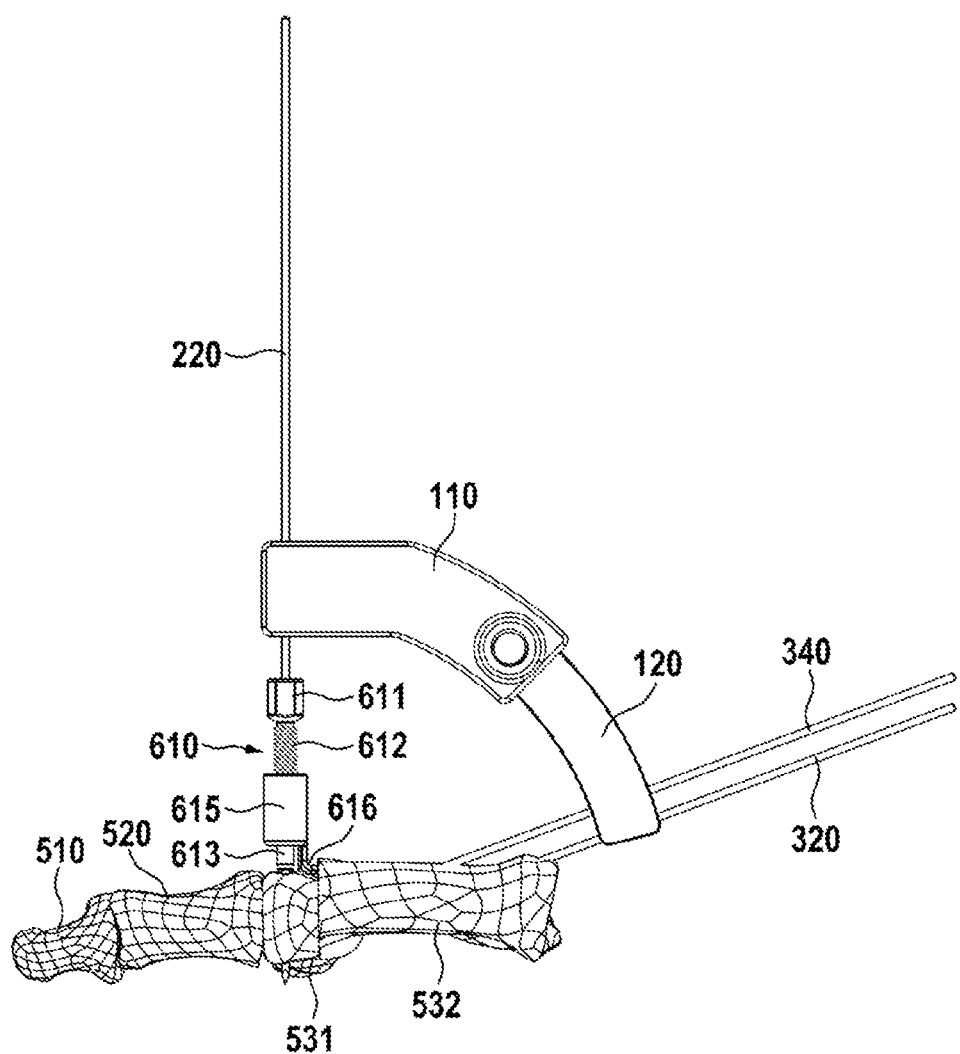
FIG. 7 shows a perspective view of a further targeting device.

FIG. 7 shows a perspective view of a further targeting device. This embodiment has a partially simplified body and a hook sleeve assembly comprising a positioning screw 610 and a hook sleeve 615 further comprising a hook. Here, at least some of the sleeves may be integrated into the body and/or extension.

Figure 8:
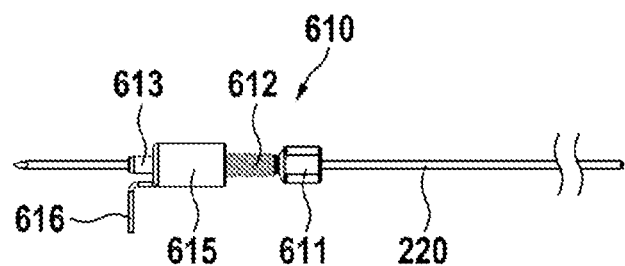
FIG. 8 shows a hook sleeve.

FIG. 8 shows a hook sleeve and a positioning screw in detail. A positioning screw 610 having an inner sleeve 613 fits on the target pin 220. The positioning screw 610 may have an outer thread 612 and may have a nut 611. The positioning screw 610 may be screwed into a hook sleeve 615. When screwed together, the sleeve assembly comprising the inner sleeve 613 and the positioning screw 610 may firmly hold at the target pin 220, which may be close to the tip of the target pin 220. The hook sleeve 615 may have a hook 616 with an extension radial to the target pin 220. The hook 616 may further have an axial extension to provide an offset in axial direction. The hook 616 may include a wire which may have a diameter of less than 2 mm or less than 1 mm and may have a length of less than 15 mm or less than 10 mm. The hook sleeve 615 may be used as an alternative to the target sleeve 210.

Figure 9:
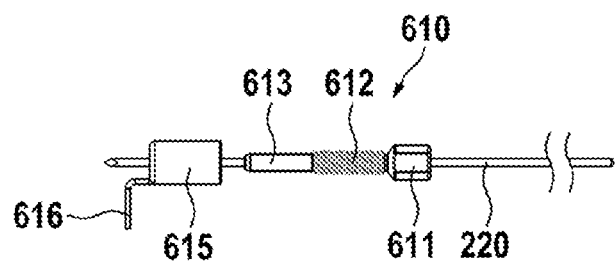
FIG. 9 shows a detailed view of a hook sleeve.

FIG. 9 shows a detailed view of a hook sleeve assembly. Here, the hook sleeve 615 and the positioning screw 610 are disassembled.

LIST OF REFERENCE NUMERALS 100 targeting device
110 device body
112 locking means
115 hollow opening
116 handle
119 extension lock
120 device extension
121 first attachment hole
122, 123, 124 attachment hole
126 holding structure
155 target area
161 target pin center axis
162 first guide wire center axis
163 intersect point
171 direction of size adjustment by the target pin
172 direction of rotational adjustment
173 direction of distance adjustment
174 direction of depth adjustment
175 direction of angulation adjustment
176 rotation angle
177 angulation angle
200 target guide
210 target sleeve
211 target sleeve channel
212 coupling section
214 window
216 gear rack
217 rack wheel
220 target pin
222 laser mark
310 first guide sleeve
311 first guide sleeve channel
312 depth scale
320 first guide wire
330 second guide sleeve
331 second channel
332 depth scale
340 second guide wire
350 third guide sleeve
360 third guide wire
410 first screw
420 second screw
500 big toe
510 distal phalanx
520 proximal phalanx
530 metatarsal bone
531, 532 metatarsal bone fragments
610 hook sleeve assembly
611 nut 612 thread
613 inner sleeve
615 hook sleeve
616 hook

What is claimed is:

1. A percutaneous targeting device comprising:
a body that is arc-shaped;
an extension including a first attachment hole and an attachment opening, the attachment opening including a second attachment hole and a third attachment hole, wherein no sidewalls are located between the second attachment hole and the third attachment hole, wherein the extension is moveable relative to the body, and a position of the extension is adjustable relative to the body to change an angle between a target pin and a first guide wire;
a targeting assembly including a target sleeve defining a target channel, the targeting assembly including a hook of a hook assembly that is configured to be inserted intramedullary into a proximal bone part of a metatarsal bone, and the metatarsal bone is split into the proximal bone part and a distal bone part;
the target pin receivable through the body and configured to be placed in the distal bone part of the metatarsal bone to reposition the distal bone part of the metatarsal bone, wherein the target pin is received through the target channel of the target sleeve of the targeting assembly,
  wherein the first attachment hole is most distal to the target pin, and the attachment opening is proximal to the target pin,
  wherein the targeting assembly is configured to hold the target pin in a fixed position relative to the targeting assembly, and
  wherein the target sleeve is configured to allow for movement of the target pin within the targeting assembly;
the first guide wire inserted through the first attachment hole and configured to be inserted into the metatarsal bone;
a first cannulated fixation screw configured to be screwed into the metatarsal bone using the first guide wire;
a second guide wire inserted through one of the second attachment hole and the third attachment hole of the attachment opening depending on a desired distance between the first guide wire and the second guide wire; and
a second cannulated fixation screw configured to be screwed into the metatarsal bone using the second guide wire.

2. The targeting device according as recited in claim 1, wherein the first cannulated fixation screw is a first non-compressive cannulated fixation screw and the second cannulated fixation screw is a second non-compressive cannulated fixation screw.

3. A percutaneous targeting device comprising:
a body;
an extension moveable relative to the body, the extension including an attachment opening including a first attachment hole and a second attachment hole, and no sidewall is located between the first attachment hole and the second attachment hole;
a targeting assembly including a target channel;
a target pin receivable through the body and configured to be placed in a distal bone part of a bone to reposition the distal bone part of the bone, wherein the target pin is received through the target channel of the targeting assembly;
a guide wire inserted through one of the first attachment hole and the second attachment hole and configured to be inserted into the bone; and
a cannulated fixation screw configured to be screwed into the bone using the guide wire;
wherein the targeting assembly includes a hook of a hook assembly configured to be inserted intramedullary into a proximal bone part of the bone.

4. The targeting device according to claim 3, wherein the bone is a metatarsal bone that is split into the distal bone part and the proximal bone part.

5. The targeting device according to claim 3, including another attachment hole that receives another guide wire.

6. The targeting device according to claim 5, wherein the guide wire is received in one of the first attachment hole and the second attachment hole depending on a desired distance between the guide wire and the another guide wire.

7. The targeting device according to claim 5, including another cannulated fixation screw configured to be screwed into the bone using the another guide wire.

8. The targeting device as recited in claim 5, wherein the another attachment hole is most distal to the target pin and the attachment opening is most proximal to the target pin.

9. The targeting device according to claim 5, wherein the guide wire and the another guide wire each have a tip and is configured to be drilled into the bone.

10. The targeting device according to claim 5, wherein the attachment opening includes a third attachment hole, and no sidewalls are located between the first attachment hole, the second attachment hole, and the third attachment hole.

11. The targeting device as recited in claim 3, wherein the targeting assembly includes a target sleeve that defines the target channel that receives the target pin.

12. The targeting device according to claim 11, wherein the target sleeve is configured to allow for movement of the target pin within the targeting assembly.

13. The targeting device according as recited in claim 3, wherein a position of the extension is adjustable relative to the body to change an angle between the target pin and the guide wire.

14. The targeting device as recited in claim 3, wherein the cannulated fixation screw is a non-compressive cannulated fixation screw.

15. The targeting device according to claim 3, wherein the targeting assembly is configured to hold the target pin in a fixed position relative to the targeting assembly.

16. The targeting device according to claim 3, wherein the target pin is a K-wire that extends axially through the targeting assembly.

17. The targeting device according to claim 3, wherein the body is arc-shaped.

18. The targeting device according to claim 3, wherein a periphery of the targeting assembly includes a window along the target channel, the target pin includes a first indicator, the body includes a second indicator, and the first and second indicators are alignable with each other at a position along the window.

19. A percutaneous targeting device comprising:
a body;
an extension moveable relative to the body, the extension including an attachment hole;
a targeting assembly including a target channel, wherein the targeting assembly includes a hook of a hook assembly configured to be inserted intramedullary into a proximal bone part of a bone;
a target pin receivable through the target channel and configured to be placed in a distal bone part of the bone to reposition the distal bone part of the bone;
a guide wire inserted through the attachment hole and configured to be inserted into the bone; and
a cannulated fixation screw configured to be screwed into the bone using the guide wire.

* * * * *